United States Patent
Klemm et al.

(10) Patent No.: US 10,271,510 B2
(45) Date of Patent: Apr. 30, 2019

(54) PETUNIA VARIETY KLEPH17342

(71) Applicant: Klemm+Sohn GmbH & Co. KG, Stuttgart (DE)

(72) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/710,831

(22) Filed: Sep. 21, 2017

(65) Prior Publication Data

US 2019/0082631 A1    Mar. 21, 2019

(51) Int. Cl.
*A01H 5/02* (2018.01)
*A01H 6/82* (2018.01)

(52) U.S. Cl.
CPC .............. *A01H 6/824* (2018.05); *A01H 5/02* (2013.01)

(58) Field of Classification Search
CPC ...................................................... A01H 6/824
See application file for complete search history.

(56) References Cited

U.S. PATENT DOCUMENTS

2017/0196177 A1* 7/2017 Klemm .................... A01H 5/02

* cited by examiner

*Primary Examiner* — David H Kruse
(74) *Attorney, Agent, or Firm* — Barbara Campbell; Cochran Freund & Young LLC

(57) ABSTRACT

A *Petunia* plant designated KLEPH17342 is disclosed. Embodiments include seeds of *Petunia* KLEPH17342, plants of *Petunia* KLEPH17342, to plant parts of *Petunia* KLEPH17342, and methods for producing a *Petunia* plant produced by crossing *Petunia* KLEPH17342 with itself or with another *Petunia* variety. Embodiments also relate to *Petunia* varieties, breeding varieties, plant parts, and cells derived from *Petunia* KLEPH17342, methods for producing other *Petunia* lines or plant parts derived from *Petunia* KLEPH17342, and the *Petunia* plants, varieties, and their parts derived from use of those methods. Embodiments further include hybrid *Petunia* seeds, plants, and plant parts produced by crossing *Petunia* KLEPH17342 with another *Petunia* variety.

23 Claims, 1 Drawing Sheet

PETUNIA VARIETY KLEPH17342

BACKGROUND

All publications cited in this application are herein incorporated by reference. *Petunia* is a species of flowering plants in the family Solanaceae.

*Petunia* can be propagated from seed, cuttings, and tissue culture. Seed, cuttings and tissue culture germination protocols for *Petunia* are well-known in the art.

*Petunia* is an important and valuable ornamental plant. Thus, a continuing goal of ornamental plant breeders is to develop plants with novel characteristics, such as color, growth habit, and hardiness. To accomplish this goal, the breeder must select and develop plants that have traits that result in superior *Petunia* varieties.

The foregoing examples of the related art and limitations related therewith are intended to be illustrative and not exclusive. Other limitations of the related art will become apparent to those of skill in the art upon a reading of the specification.

BRIEF DESCRIPTION OF THE FIGURE

FIG. 1 shows the overall plant habit of the plant grown in a pot.

SUMMARY

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

According to one embodiment, there is provided a *Petunia* plant which is valued as breeding line enabling the development of superior ornamental *Petunia* plants.

Another embodiment discloses a *Petunia* plant, wherein a sample of representative sample of live plant tissue of said *Petunia* is deposited with NCIMB.

Another embodiment relates to tissue culture produced from protoplasts or cells from the *Petunia* plants disclosed in the subject application, wherein said cells or protoplasts are produced from a plant part selected from the group consisting of pollen, ovules, embryos, protoplasts, meristematic cells, callus, leaves, anthers, cotyledons, hypocotyl, pistils, roots, root tips, flowers, seeds, petiole, and stems.

Another embodiment relates to a tissue or cell culture of regenerable cells produced from the plant of KLEPH17342 and a *Petunia* plant regenerated from the tissue or cell culture of KLEPH17342.

Another embodiment relates to a method of vegetatively propagating the plant of KLEPH17342, comprising the steps of: collecting tissue or cells capable of being propagated from a plant of KLEPH17342; cultivating said tissue or cells of the prior step to obtain proliferated shoots or plantlets; and rooting said proliferated shoots or plantlets to obtain rooted shoots or rooted plantlets.

A further embodiment relates to a method for producing an $F_1$ *Petunia* seed, wherein the method comprises crossing a KLEPH17342 plant with a different *Petunia* plant and harvesting the resultant $F_1$ *Petunia* seed.

A further embodiment relates to a method for developing a *Petunia* plant in a *Petunia* plant breeding program, comprising applying plant breeding techniques comprising recurrent selection, mass selection, hybridization, open-pollination breeding, backcrossing, pedigree breeding, or genetic marker enhanced selection to the *Petunia* plant of KLEPH17342, or its parts, wherein application of said techniques results in development of a *Petunia* plant.

A further embodiment relates to a method of introducing a mutation into the genome of a KLEPH17342 plant, said method comprising inducing a mutation to the plant, or plant part thereof, of KLEPH17342, wherein said mutation is selected from the group consisting of ionizing radiation, chemical mutagens, targeting induced local lesions in genomes, zinc finger nuclease mediated mutagenesis, meganucleases, and gene editing, and wherein the resulting plant comprises at least one genome mutation and producing plants therefrom.

A further embodiment relates to a naturally-occurring genetic mutation of KLEPH17342, wherein said mutation is comprised from the group consisting of a single cell mutation, branch mutation, or a whole-plant mutation and a plant produced therefrom.

A further embodiment relates to a method of genetically modifying a plant of KLEPH17342, wherein the resulting plant comprises at least one new trait when compared to KLEPH17342 and the resulting plant produced therefrom.

In addition to the exemplary aspects and embodiments described above, further aspects and embodiments will become apparent by study of the following descriptions.

Definitions

In the description and tables herein, a number of terms are used. In order to provide a clear and consistent understanding of the specification and claims, including the scope to be given such terms, the following definitions are provided:

Allele. Allele is any of one or more alternative forms for a gene.

Gene. As used herein, "gene" refers to a segment of nucleic acid.

Progeny. As used herein, the descendants of one or more of the parental lines and includes an $F_1$ *Petunia* plant produced from the cross of two *Petunia* plants where at least one plant includes a *Petunia* plant disclosed herein and progeny further includes, but is not limited to, subsequent $F_2$, $F_3$, $F_4$, $F_5$, $F_6$, $F_7$, $F_8$, $F_9$, and $F_{10}$ generational crosses with the recurrent parental line.

RHS. RHS refers to the acronym for Royal Horticultural Society that publishes a color chart used in the plant industry. All RHS colors referred to herein are from the RHS $5^{th}$ Edition.

DETAILED DESCRIPTION

*Petunia* variety KLEPH17342 disclosed in the present application has shown uniformity and stability, as described in the following section. *Petunia* variety KLEPH17342 disclosed in the present application has been asexually reproduced, and it is well-known in the art, that KLEPH17342 can be reproduced sexually.

Origin of KLEPH17342

KLEPH17342 originated from a cross-pollination conducted in July 2014 in Latina, Italy between the proprietary female *Petunia* variety 'PH-2014-0443' (referenced in U.S. Publication No. 20170196177, now U.S. Pat. No. 9,913,438 entitled "*Petunia* plants having a unique flower color pattern") having a red-purple flower color with white spots, and the proprietary male *Petunia* variety 'PH-2012-3051' (unpatented) having a red-purple flower color.

The seeds from the cross were sown and plants were grown in a greenhouse for evaluation, where an individual plant designated KLEPH17342 was selected from the group of plants in April 2015 in Latina, Italy having a plurality of spots on its flowers, as shown in FIG. 1. In May 2015, KLEPH17342 was first vegetatively propagated by terminal tip cuttings in Latina, Italy. KLEPH17342 was found to reproduce true to type in successive generations of asexual propagation via tissue culture and terminal tip cuttings.

The data which define these characteristics were collected from asexual reproductions carried out in Latina, Italy. Data was collected on plants grown 7-weeks from cultivation from potting in a plastic greenhouse in Latina, Italy in April 2017. Color references are to The R.H.S. Colour Chart of The Royal Horticultural Society of London (R.H.S.), 5$^{th}$ edition (2007).

TABLE 1

VARIETY DESCRIPTION INFORMATION

Classification:
Family: *Solanaceae*
Botanical: *Petunia hybrida*
Common: Petunia
Designation: 'KLEPH17342'
Parentage:
Female parent: The proprietary female *Petunia* variety 'PH-2014-0443' (unpatented)
Male parent: The proprietary male *Petunia* variety 'PH-2012-3051' (unpatented)
Plant:
Vigor: Medium/compact vigor
Habit: Mounding/semi-trailing
Height (from top of soil): 10.0 cm
Width (horizontal plant diameter): 25.0 cm
Propagation: Terminal tip cuttings and tissue culture
Time to produce a finished flowering plant: About 11 weeks in the winter under short day conditions, and 5 weeks in the spring
Time to initiate and develop roots: 2 to 3 weeks
Root description: Moderate density, moderate branching, white roots
Stems:
Average number (basal): 12 to 15
Length of basal branches (from the base of the stem to the tip): 11.0 cm
Internode length: 1.4 cm to 2.5 cm
Diameter of branches (from midpoint): 0.4 cm
Stem color: Varies between RHS 145A and RHS 145B
Anthocyanin: Absent
Texture: Pubescent
Leaves:
Arrangement: Alternate
Length: 8.0 cm to 8.5 cm
Width: 3.5 cm
Shape: Obovate to spatulate
Apex: Broad acute
Base: Attenuate
Margin: Entire
Immature leaf color:
    Upper surface: RHS 137
    Lower surface: RHS 147B
Mature leaf color:
    Upper surface: RHS 137B
    Lower surface: RHS 138B
Texture (both upper and lower surfaces): Pubescent
Venation pattern: Arcuate
Venation color:
    Upper surface: RHS 144A
    Lower surface: RHS 144A
Petioles:
    Length: 1.5 cm
    Diameter: 3.5 cm
    Color: RHS 145A
    Texture: Pubescent
Flower buds:
Shape: Irregular oblong
Length: 2.5 cm to 4.5 cm
Diameter: 0.5 cm to 0.8 cm
Color at tight bud: RHS N144C at the base, RHS 145C at the apex TABLE 1-continued

VARIETY DESCRIPTION INFORMATION

Texture: Pubescent
Inflorescence:
Blooming habit (flowering season): Continuously flowering during spring and summer
Inflorescence type: Sympodial, with monochasial growth
Number of flowers per node: 1
Lastingness of individual blooms on the plant: About 1 week
Fragrance: Not detected
Flowers:
    Arrangement: Composed of 5 petals fused at the base
    Diameter (flower face): 7.0 cm
    Depth (total length of flower): 6.0 cm to 6.5 cm
    Throat/Funnel:
        Length: 2.5 cm to 2.8 cm
        Diameter (at opening): 1.0 cm to 1.4 cm
        Texture:
            Inner surface: Smooth
            Outer surface: Pubescent
        Color:
            Inner surface: RHS 76D and RHS 77A
            Outer surface: RHS 76C and RHS 145B
    Petals:
        Color of petals, mature flower (fully opened):
            Upper surface: RHS N74A and RHS NN155C spots
            Lower surface: From RHS 75A at the base to RHS N74C at the margin with RHS NN155A spots
        Apex: Slightly mucronate
        Base: Fused
        Shape: Funnelform
        Margin: Entire
        Strength of waviness: Medium
        Degree of lobation: Medium
    Calyx arrangement: Actinomorphic, composed of 5 sepals
        Sepals:
            Color:
                Upper surface: RHS N137C
                Lower surface: RHS 147B
            Length: 2.0 cm to 2.5 cm
            Width: 0.5 cm to 0.8 cm
            Shape: Spatulate
            Apex: Slightly mucronate
            Base: Attenuate
            Margin: Entire
            Texture (both upper and lower surfaces): Slightly pubescent
    Pedicels:
        Color: RHS 144A
        Length: 3.5 cm to 4.0 cm
        Diameter: 0.2 cm
        Texture: Pubescent
Reproductive organs:
Stamens:
    Quantity: 5
    Shape: Needle with elliptic head
    Filament:
        Length: 2.0 cm to 2.2 cm
        Diameter: 0.05 cm
    Anther:
        Shape: Ovate
        Color: RHS 145C
        Length: 0.1 cm
        Diameter: 0.1 cm
    Pollen:
        Color: RHS 150D
        Amount: Moderate
Pistils:
    Quantity per flower: 1
    Length: 2.3 cm
    Stigma color: RHS 143A
    Style color: RHS 145C
Disease and pest/insect resistance: No disease and pest/insect resistance observed.

Further Embodiments

Breeding with *Petunia* KLEPH17342

The goal of ornamental plant breeding is to develop new, unique and superior ornamental plants. The breeder initially selects and crosses two or more parental lines, followed by repeated selfing and selection, producing many new genetic combinations. The breeder can theoretically generate billions of different genetic combinations via crossing, selection, selfing and mutations. Therefore, a breeder will never develop the same genetic variety, having the same traits from the exact same parents.

Each year, the plant breeder selects the germplasm to advance to the next generation. This germplasm is grown under unique and different geographical, climatic and soil conditions and further selections are then made during and at the end of the growing season. The varieties that are developed are unpredictable because the breeder's selection occurs in unique environments with no control at the DNA level, and with millions of different possible genetic combinations being generated. A breeder of ordinary skill in the art cannot predict the final resulting lines he develops, except possibly in a very gross and general fashion. The same breeder cannot produce the same variety twice by using the same original parents and the same selection techniques. This unpredictability results in the expenditure of large amounts of research monies to develop superior Petunia varieties.

Breeding programs combine desirable traits from two or more varieties or various broad-based sources into breeding pools from which varieties are developed by selfing and selection of desired phenotypes. Pedigree breeding is used commonly for the improvement of self-pollinating plants. Two parents that possess favorable, complementary traits are crossed to produce an $F_1$. An $F_2$ population is produced by selfing one or several $F_1$s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Using Petunia KLEPH17342 to Develop Other Plants

KLEPH17342 can also provide a source of breeding material that may be used to develop new Petunia plants and varieties. Plant breeding techniques known in the art and used in a Petunia plant breeding program include, but are not limited to, recurrent selection, mass selection, bulk selection, hybridization, mass selection, backcrossing, pedigree breeding, open-pollination breeding, restriction fragment length polymorphism enhanced selection, genetic marker enhanced selection, making double haploids, mutagenesis and transformation. Often combinations of these techniques are used. There are many analytical methods available to evaluate a new variety. The oldest and most traditional method of analysis is the observation of phenotypic traits, but genotypic analysis may also be used.

Additional Breeding Methods

Any plants produced using KLEPH17342 as at least one parent are also an embodiment. These methods are well-known in the art and some of the more commonly used breeding methods are described herein. Descriptions of breeding methods can be found in one of several reference books (e.g., Allard, "Principles of Plant Breeding" (1999); Vainstein, "Breeding for Ornamentals: Classical and Molecular Approaches," Kluwer Academic Publishers (2002); Callaway, "Breeding Ornamental Plants," Timber Press (2000); and Bragdø, Marie, "Inter-specific Crosses in Lupinus: Cytology and Inheritance of Flower Color," Institute of Genetics and Plant Breeding, Agricultural College of Norway, Vollebekk, Norway (Sep. 28, 1956).

Breeding steps that may be used in the Petunia plant breeding program can include for example, pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

As used herein, the term "plant" includes plant cells, plant protoplasts, plant cell tissue cultures from which Petunia plants can be regenerated, plant calli, plant clumps, and plant cells that are intact in plants or parts of plants, such as pollen, ovules, embryos, protoplasts, meristematic cells, callus, leaves, anthers, cotyledons, hypocotyl, pistils, roots, root tips, seeds, flowers, petiole, shoot, or stems and the like.

Pedigree Breeding

Pedigree breeding starts with the crossing of two genotypes, such as KLEPH17342 and another different Petunia having one or more desirable characteristics. If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection. Typically, in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety. Preferably, the developed variety comprises homozygous alleles at about 95% or more of its loci.

Backcross Breeding

Backcross breeding has been used to transfer genes for a simply inherited, highly heritable trait into a desirable homozygous variety or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent and the desirable trait transferred from the donor parent.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good commercial characteristics and yet lacks that desirable trait or traits. However, the same procedure can be used to move the progeny toward the genotype of the recurrent parent, but at the same time retain many components of the nonrecurrent parent by stopping the backcrossing at an early stage and proceeding with selfing and selection. For example, a Petunia plant may be crossed with another variety to produce a first-generation progeny plant. The first-generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new Petunia varieties.

Therefore, another embodiment is a method of making a backcross conversion of KLEPH17342, comprising the steps of crossing KLEPH17342 with a donor plant comprising a desired trait, selecting an $F_1$ progeny plant comprising the desired trait, and backcrossing the selected F$_1$ progeny plant to KLEPH17342. This method may further comprise the step of obtaining a molecular marker profile of KLEPH17342 and using the molecular marker profile to select for a progeny plant with the desired trait and the molecular marker profile of KLEPH17342.

Recurrent Selection and Mass Selection

Recurrent selection is a method used in a plant breeding program to improve a population of plants. KLEPH17342 is suitable for use in a recurrent selection program. The method entails individual plants cross-pollinating with each other to form progeny. The progenies are grown and the superior progenies selected by any number of selection methods, which include individual plant, half-sib progeny, full-sib progeny, and selfed progeny. The selected progenies are cross-pollinated with each other to form progeny for another population. This population is planted and again superior plants are selected to cross-pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic variety. A synthetic variety is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Also, instead of self-pollination, directed pollination could be used as part of the breeding program.

Mass and recurrent selections can be used to improve populations of either self- or cross-pollinating plants. A genetically variable population of heterozygous individuals is either identified, or created, by intercrossing several different parents. The best plants are selected based on individual superiority, outstanding progeny, or excellent combining ability. The selected plants are intercrossed to produce a new population in which further cycles of selection are continued.

Mutation Breeding

Mutation breeding is another method of introducing new traits into *Petunia* KLEPH17342. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions (also known as somaclonal variation), ionizing radiation, such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm); chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates such as ethyl methanesulfonate, sulfones, lactones), sodium azide, hydroxylamine, nitrous acid, methylnitrilsourea, or acridines; TILLING (targeting induced local lesions in genomes), where mutation is induced by chemical mutagens and mutagenesis is accompanied by the isolation of chromosomal DNA from every mutated plant line or seed and screening of the population of the seed or plants is performed at the DNA level using advanced molecular techniques; zinc finger nucleases. Once a desired trait is observed through mutagenesis the trait may then be incorporated into existing germplasm by traditional breeding techniques. Details of mutation breeding can be found in Vainstein, "Breeding for Ornamentals: Classical and Molecular Approaches," Kluwer Academic Publishers (2002); Sikora, Per, et al., "Mutagenesis as a Tool in Plant Genetics, Functional Genomics, and Breeding" *International Journal of Plant Genomics.* 2011 (2011); 13 pages; Petilino, Joseph F. "Genome editing in plants via designed zinc finger nucleases" *In Vitro Cell Dev Biol Plant.* 51(1): pp. 1-8 (2015); and Daboussi, Fayza, et al. "Engineering Meganuclease for Precise Plant Genome Modification" in Advances in New Technology for Targeted Modification of Plant Genomes. Springer Science+Business. pp 21-38 (2015). In addition, mutations created in other *Petunia* plants may be used to produce a backcross conversion of *Petunia* that comprises such mutation.

Mutations that occur spontaneously can also be known as naturally-occurring mutations. These types of mutations are further known as sports, breaks, or chimeras and can be comprised of single cell mutations, branch mutations, or whole plant mutations. Any one of these mutations can change one or more phenotypic characteristics when compared to the original plant. Therefore, another embodiment of includes a naturally-occurring genetic mutation of the plant of KLEPH17342, wherein said mutation is comprised from the group consisting of a single cell mutation, branch mutation, or a whole-plant mutation and plants derived from said naturally-occurring mutation or mutations.

Gene Editing Using CRISPR

Targeted gene editing can be done using CRISPR/Cas9 technology (Saunders & Joung, *Nature Biotechnology,* 32, 347-355, 2014). CRISPR is a type of genome editing system that stands for Clustered Regularly Interspaced Short Palindromic Repeats. This system and CRISPR-associated (Cas) genes enable organisms, such as select bacteria and archaea, to respond to and eliminate invading genetic material. Ishino, Y., et al. *J. Bacteriol.* 169, 5429-5433 (1987). These repeats were known as early as the 1980s in *E. coli*, but Barrangou and colleagues demonstrated that *S. thermophilus* can acquire resistance against a bacteriophage by integrating a fragment of a genome of an infectious virus into its CRISPR locus. Barrangou, R., et al. *Science* 315, 1709-1712 (2007). Many plants have already been modified using the CRISPR system. See for example, U.S. Application Publication No. WO2014068346 (Gyorgy et al., Identification of a *Xanthomonas euvesicatoria* resistance gene from pepper (*Capsicum annuum*) and method for generating plants with resistance); Martinelli, F. et al., "Proposal of a Genome Editing System for Genetic Resistance to Tomato Spotted Wilt Virus" *American Journal of Applied Sciences* 2014; Noman, A. et al., "CRISPR-Cas9: Tool for Qualitative and Quantitative Plant Genome Editing" *Frontiers in Plant Science* Vol. 7 Nov. 2016; and "Exploiting the CRISPR/Cas9 System for Targeted Genome Mutagenesis in *Petunia*" *Science Reports* Volume 6: February 2016.

Gene editing can also be done using crRNA-guided surveillance systems for gene editing. Additional information about crRNA-guided surveillance complex systems for gene editing can be found in the following documents, which are incorporated by reference in their entirety: U.S.

Application Publication No. 2010/0076057 (Sontheimer et al., Target DNA Interference with crRNA); U.S. Application Publication No. 2014/0179006 (Feng, CRISPR-CAS Component Systems, Methods, and Compositions for Sequence Manipulation); U.S. Application Publication No. 2014/0294773 (Brouns et al., Modified Cascade Ribonucleoproteins and Uses Thereof); Sorek et al., *Annu. Rev. Biochem.* 82:273-266, 2013; and Wang, S. et al., *Plant Cell Rep* (2015) 34: 1473-1476. Therefore, it is another embodiment to use the CRISPR system on *Petunia* KLEPH17342 to modify traits and resistances or tolerances to pests, herbicides, diseases, and viruses.

Additional Methods of Transformation

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformant plants obtained with the protoplasm of the subject *Petunia* KLEPH17342 plants are intended to be within the scope of the embodiments of the application.

Single-Gene Conversions

When the term *Petunia* KLEPH17342 plant is used in the context of an embodiment of the present application, this also includes any single gene conversions of *Petunia* KLEPH17342. The term single gene converted plant as used herein refers to those *Petunia* plants which are developed by a plant breeding technique called backcrossing wherein essentially all of the desired morphological and physiological characteristics of a variety are recovered in addition to the single gene transferred into the variety via the backcrossing technique. Backcrossing methods can be used with one embodiment of the present application to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, or more times to the recurrent parent. The parental *Petunia* plant that contributes the gene for the desired characteristic is termed the nonrecurrent or donor parent. This terminology refers to the fact that the nonrecurrent parent is used one time in the backcross protocol and therefore does not recur. The parental *Petunia* plant to which the gene or genes from the nonrecurrent parent are transferred is known as the recurrent parent as it is used for several rounds in the backcrossing protocol (Poehlman & Sleper (1994). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a *Petunia* plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially important trait or traits to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred.

Many single gene traits have been identified that are not regularly selected for in the development of a new variety but that can be improved by backcrossing techniques. These traits are well-known in the art.

Introduction of a New Trait or Locus into *Petunia* KLEPH17342

*Petunia* KLEPH17342 represents a new base of genetics into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of *Petunia* KLEPH17342

A backcross conversion of *Petunia* KLEPH17342 occurs when DNA sequences are introduced through backcrossing (Allard, "Principles of Plant Breeding" (1999) with *Petunia* KLEPH17342 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Openshaw, S. J., et al., Marker-assisted Selection in Backcross Breeding, Proceedings Symposium of the Analysis of Molecular Data, *Crop Science Society of America*, Corvallis, Oreg. (August 1994), where it is demonstrated that a backcross conversion can be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. See, Allard, "Principles of Plant Breeding" (1999). Desired traits that may be transferred through backcross conversion include, but are not limited to, sterility (nuclear and cytoplasmic), fertility restoration, drought tolerance, nitrogen utilization, ornamental features, disease resistance (bacterial, fungal, or viral), insect resistance, and herbicide resistance. In addition, an introgression site itself, such as an FRT site, Lox site, or other site-specific integration site, may be inserted by backcrossing and utilized for direct insertion of one or more genes of interest into a specific plant variety. In some embodiments, the number of loci that may be backcrossed into *Petunia* KLEPH17342 is at least 1, 2, 3, 4, or 5, and/or no more than 6, 5, 4, 3, or 2.

The backcross conversion may result from either the transfer of a dominant allele or a recessive allele. Selection of progeny containing the trait of interest is accomplished by direct selection for a trait associated with a dominant allele. Transgenes or genes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

In addition, the above process and other similar processes described herein may be used to produce first generation progeny *Petunia* seed by adding a step at the end of the process that comprises crossing *Petunia* KLEPH17342 with the introgressed trait or locus with a different plant and harvesting the resultant first generation progeny seed.

Molecular Techniques Using *Petunia* KLEPH17342

The advent of new molecular biological techniques has allowed the isolation and characterization of genetic elements with specific functions. Traditional plant breeding has principally been the source of new germplasm, however, advances in molecular technologies have allowed breeders to provide varieties with novel and much wanted commercial attributes. Molecular techniques such as transformation are popular in breeding ornamental plants and well-known in the art. See Vainstein, "Breeding for Ornamentals: Classical and Molecular Approaches," Kluwer Academic Publishers (2002).

Breeding with Molecular Markers

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses. Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs), may be used in plant breeding methods utilizing *Petunia* KLEPH17342. See Vainstein, "Breeding for Ornamentals: Classical and Molecular Approaches," Kluwer Academic Publishers (2002).

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome. See for example, Fletcher, Richard S., et al., "QTL analysis of root morphology, flowering time, and yield reveals trade-offs in response to drought in *Brassica napus*" *Journal of Experimental Biology.* 66 (1): 245-256 (2014). QTL markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Tissue Culture

Further reproduction of the variety can occur by tissue culture and regeneration. Tissue culture of various tissues of ornamental plants and *Petunia* KLEPH17342 and regeneration of plants therefrom is well-known and widely published. For example, reference may be had to do Valla Rego, Luciana et al., *Crop Breeding and Applied Technology.* 1(3): 283-300 (2001); Komatsuda, T., et al., *Crop Sci.,* 31:333-337 (1991); Stephens, P. A., et al., *Theor. Appl. Genet.,* 82:633-635 (1991); Komatsuda, T., et al., *Plant Cell, Tissue and Organ Culture,* 28:103-113 (1992); Dhir, S., et al., *Plant Cell Reports,* 11:285-289 (1992); Pandey, P., et al., *Japan J Breed.,* 42:1-5 (1992); and Shetty, K., et al., *Plant Science,* 81:245-251 (1992). Thus, another embodiment is to provide cells which upon growth and differentiation produce *Petunia* plants having the physiological and morphological characteristics of *Petunia* KLEPH17342 described in the present application.

Regeneration refers to the development of a plant from tissue culture. The term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as pollen, ovules, embryos, protoplasts, meristematic cells, callus, leaves, anthers, cotyledons, hypocotyl, pistils, roots, root tips, flowers, seeds, petiole, shoot, or stems, and the like. Means for preparing and maintaining plant tissue culture are well-known in the art.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

One or more aspects may be embodied in other specific forms without departing from its spirit or essential characteristics. The described embodiments are to be considered in all respects only as illustrative and not restrictive. The scope of the embodiments is, therefore, indicated by the appended claims rather than by the foregoing description. All changes which come within the meaning and range of equivalency of the claims are to be embraced within their scope. The foregoing discussion of the embodiments has been presented for purposes of illustration and description. The foregoing is not intended to limit the embodiments to the form or forms disclosed herein. In the foregoing Detailed Description for example, various features of the embodiments are grouped together in one or more embodiments for the purpose of streamlining the disclosure. This method of disclosure is not to be interpreted as reflecting an intention that the claimed embodiments require more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment.

Moreover, though the description of the embodiments has included description of one or more embodiments and certain variations and modifications, other variations and modifications are within the scope of the embodiments (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

The use of the terms "a," "an," and "the," and similar referents in the context of describing the embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the embodiments unless otherwise claimed. No language in the specification should be construed as indicating any non-claimed element as essential to the practice one or more embodiments.

DEPOSIT INFORMATION

A representative sample of proprietary Petunia KLEPH17342 plant tissue of the Klemm+Sohn GmbH & Co. KG disclosed above and recited in the appended claims has been made with the Provasoli-Guillard National Center for Marine Algae and Microbiota, Bigelow Laboratory for National Sciences, 60 Bigelow Drive, East Boothbay, Me. 04544. The date of deposit was May 10, 2018. The NCMA No. is 201805003. The deposit of plant tissue was taken from the same deposit maintained by Klemm+Sohn GmbH & Co. KG since prior to the filing date of this application. The deposit will be maintained in the NCMA depository for a period of 30 years, or 5 years after the most recent request, or for the enforceable life of the patent, whichever is longer, and will be replaced if necessary during that period. Upon issuance, all restrictions on the availability to the public of the deposit will be irrevocably removed consistent with all of the requirements of 37 C.F.R. §§ 1.801-1.809.

What is claimed is:

1. A plant of *Petunia* variety KLEPH17342, having a spotted flower color pattern, wherein a representative sample of plant tissue of said variety was deposited under NCMA No. 201805003.

2. A plant, or a plant part thereof, produced by growing a plant of *Petunia* variety KLEPH17342, wherein a representative sample of plant tissue of said variety was deposited under NCMA No. 201805003, and wherein the plant or plant part comprises at least one cell of *Petunia* variety KLEPH17342.

3. A *Petunia* plant, or part thereof, having all of the physiological and morphological characteristics of the *Petunia* plant of claim 1.

4. A tissue or cell culture of regenerable cells produced from the plant or plant part of claim 2.

5. A *Petunia* plant regenerated from the tissue or cell culture of claim 4, wherein said plant has all of the morphological and physiological characteristics of *Petunia* variety KLEPH17342 listed in Table 1.

6. A method of vegetatively propagating the plant of claim 1, comprising the steps of:
   collecting tissue or cells capable of being propagated from said plant;
   cultivating said tissue or cells to obtain proliferated shoots or plantlets; and
   rooting said proliferated shoots or plantlets to obtain rooted shoots or rooted plantlets.

7. A *Petunia* plant produced by growing the rooted shoots or rooted plantlets of claim 6.

8. A method for producing a seed or an embryo, wherein the method comprises crossing *Petunia* variety KLEPH17342, having a spotted flower color pattern, wherein a representative sample of plant tissue of said variety was deposited under NCMA No. 201805003, with a different plant and harvesting the resultant seed or embryo.

9. A method of determining the genotype of the *Petunia* plant of claim 1, wherein said method comprises obtaining a sample of nucleic acids from said plant and detecting in said nucleic acids a plurality of polymorphisms.

10. A method of introducing a mutation into the genome of a KLEPH17342 plant, said method comprising mutagenesis of the plant, or plant part thereof, of claim 1, wherein said method of mutagenesis is selected from the group consisting of temperature, long term seed storage, somaclonal variation, radiation, chemical agents, targeting induced local lesions in genomes, site-directed mutagenesis, and genome editing, and wherein the resulting plant comprises at least one genome mutation.

11. A method of genetically modifying the plant of claim 1, wherein said genetic modification is selected from gene *agrobacterium*-mediated gene transfer, protoplast transformation, or biolistic transformation.

12. A plant produced by the method of claim 11, wherein said plant has the spotted flower color pattern.

13. A method for producing a seed or embryo, wherein the method comprises selfing the *Petunia* variety KLEPH17342, having a spotted flower color pattern, wherein a representative sample of plant tissue of said variety was deposited under NCMA No. 201805003, and harvesting the resultant seed or embryo.

14. A plant produced by growing the seed or embryo produced by the method of claim 13, wherein said plant has the spotted color flower pattern.

15. A method for developing a *Petunia* plant having a spotted flower color pattern, wherein said method comprises applying plant breeding techniques to the plant of *Petunia* variety KLEPH17342, having a spotted flower color pattern, wherein a representative sample of plant tissue of said variety was deposited under NCMA No. 201805003, to produce a plant having a spotted flower color pattern.

16. The method of claim 15, wherein said plant breeding technique is recurrent selection.

17. The method of claim 15, wherein said plant breeding technique is mass selection.

18. The method of claim 15, wherein said plant breeding technique is hybridization.

19. The method of claim 15, wherein said plant breeding technique is open-pollination.

20. The method of claim 15, wherein said plant breeding technique is backcrossing.

21. The method of claim 15, wherein said plant breeding technique is pedigree breeding.

22. The method of claim 15, wherein said plant breeding technique is mutation breeding, and wherein said mutation selected is naturally occurring or artificially induced.

23. The method of claim 15, wherein said plant breeding technique is genetic marker enhanced selection.

\* \* \* \* \*